United States Patent [19]
Weiland et al.

[11] Patent Number: 6,057,370
[45] Date of Patent: *May 2, 2000

[54] ENHANCEMENT OF INSECTICIDES ACTIVITY ON BT COTTON

[76] Inventors: Robert Timothy Weiland, 55 Abbey Ct., Cheshire, Conn. 06410; Paul Thomas McDonald, 43 Mirey Dam Rd., Middlebury, Conn. 06762; Kevin Leo Kelley, 115 Campville Rd., Northfield, Conn. 06778

[*] Notice: This patent issued on a continued prosecution application filed under 37 CFR 1.53(d), and is subject to the twenty year patent term provisions of 35 U.S.C. 154(a)(2).

[21] Appl. No.: 08/863,387

[22] Filed: May 27, 1997

Related U.S. Application Data

[60] Provisional application No. 60/018,880, May 30, 1996.

[51] Int. Cl.[7] ................................................. A01N 47/28
[52] U.S. Cl. .................................................. 514/594
[58] Field of Search ............................................. 514/594

[56] References Cited

U.S. PATENT DOCUMENTS

| | | | |
|---|---|---|---|
| 5,359,142 | 10/1994 | McPherson et al. | 800/205 |
| 5,424,200 | 6/1995 | McPherson et al. | 435/70.1 |

FOREIGN PATENT DOCUMENTS 1325191  12/1993  Canada .

OTHER PUBLICATIONS

Chemical Abstracts, vol. 125, No. 13 (1996) Elzen: "Evaluation of Beet Armyworm Tolerance to Insecticides and Response to Insect Growth Regulators" and Southwest Entomol. vol. 21, No. 2 (1996).

Chemical Abstracts, vol. 106, No. 23 (1987) Novotny et al.: "Synergism of Biological and Chemical Insecticides in the Control of Caterpillars of Gypsy Moth *Lymantria Dispar*" and Lesnictvi, vol. 32, No. 12 (1986).

Biological Abstracts, vol. 67 (1979) Canivet et al. "Mixtures of *Bacillus Thuringiensis* with Low Doses of Chemical with Insecticides. Effects on *Euproctis–Chrysorrhoea*" and Z Angew Entomol, vol. 86, No. (1978).

Biological Abstracts, vol. 86 (1988) Novotny: "The Effectiveness of Tank–Mix Application of Nomolt and Microbial Preparation in the Control of the Caterpillars of *Lymantria–Dispar* L. Lepidoptera Lymantriidae" and Lesnictvi, vol. 34, No. 6 (1988).

Tomlin, "The Pesticide Manual" 10th ed. pp. 333–335.

*Primary Examiner*—Allen J. Robinson
*Attorney, Agent, or Firm*—Raymond D. Thompson; Paul Grandinetti

[57] ABSTRACT

A method for controlling insects of Lepidoptera on a genetically altered cotton plant having incorporated therein a gene derived from *Bacillus thuringiensis* (Bt) which codes for and expresses a protein having pesticide activity comprising the steps of applying to the foliage of said genetically altered cotton plant a pesticidally active amount of certain substituted benzoyl urea compounds.

8 Claims, No Drawings

ENHANCEMENT OF INSECTICIDES ACTIVITY ON BT COTTON

This application claims benefit of U.S. Provisional Application Ser. No. 60/018,880, filed May 30, 1996.

BACKGROUND OF THE INVENTION

The present invention is directed to a method for controlling beet armyworm (*Spodoptera exigua*) and other Lepidopteran pests on a genetically altered cotton plant whose genome makeup includes a gene derived from *Bacillus thuringiensis* (Bt). More specifically, when applied to plants which express a microbially derived protein toxic to certain insect species, activity of pesticides of structural formula (I) below, is markedly enhanced against other insects.

BACKGROUND ART

Transgenic plant varieties are being developed which express resistance to certain specific insect species. Cotton with a gene derived from *Bacillus thuringiensis* (Bt) was designed to be pesticidal to *Heliothis virescens* (tobacco budworm), *Helicoverpa zea* (cotton bollworm), *Pectinophora gossypiella* (pink bollworm), *Helicoverpa punctigera*, and *Helicoverpa armigera*.

An example of these genetically engineered cotton varieties are those described in U.S. Pat. No. 5,322,938 to McPherson et al having a gene derived from *Bacillus thuringiensis* (Bt) which codes for a protein having pesticide activity on tobacco budworm, cotton bollworm, and pink bollworm. However, it is becoming apparent in field conditions these new varieties are not effective against other destructive pest species. For example, in an article appearing in *Florida Entomologist* 77(4), pp 454–9, December 1994, Burris et al describe at pages 458–9 that there are no significant differences in leaf area consumed, mortality or pupal weights by the beet armyworm in both Bt cotton and non-gene transformed cotton. Therefore, it may be concluded that the entomology state of the art is that the Bt cotton should have no significant effect on the beet armyworm.

Leaf-feeding larvae and leafminers in forestry, top fruit, citrus, field crops, cotton, soybeans and horticultural crops are controlled effectively by insecticides exemplified by Formula (I) below, most notably, diflubenzuron. The mode of activity is as an insect growth regulator (IGR). Pesticidally formulated compounds of Formula (I) affect the formation and deposition of chitin, a primary component of an insect's outer skin (exoskeleton) upon molting from one stage to the next. The new underlying exoskeleton ruptures and the insect dies.

Substituted benzoylureas of structural formula (I) are pesticidal to other foliage feeding insects which are not controlled by this Bt toxin. Some examples of pests controlled by compounds of Formula (I) including diflubenzuron are *Lymantria dispar, Anticarsia gemmatalia, Psylia simulans, Spodoptera exigua*, and *Phyllocoptruta oleivera*. Compounds of Formula (I) also control *Aedes aegypti, Leptinotarsa decemlineata, Pieris brassica, Musca domestica* and *Schistocerca gregaria* very effectively.

Control of several of these species is of great economic importance in agriculture. For example, *Spodoptera exigua* is commonly known as beet armyworm and is quite injurious on cotton and is not controlled in Bt cotton.

This invention unexpectedly finds that substituted benzoylureas of structural formula (I) have a significantly enhanced pesticidal activity on the beet armyworm in Bt cotton as compared to regular (non-Bt) cotton. The synergistic pesticidal activity of substituted benzoylureas of structural formula (I) with Bt cotton is an example of synergy that is completely unexpected.

This invention demonstrates that substituted benzoylureas of structural formula (I) show an enhanced, synergistic pesticidal effect when applied to Bt cotton compared to regular cotton on such foliar feeding insects as the beet armyworm. As will be seen, this synergistic effect is surprising and unexpected since the earlier discussed Burris et al publication would lead one to believe there should be no difference between the results for Bt cotton and conventional cotton (non-gene modified) with regard to beet armyworm control. Substituted benzoylureas of structural formula (I) are found to be effective in protecting cotton from the beet armyworm. It also has little or no effect on a wide range of beneficial species such as braconid wasps, big eyes bugs, minute pirate bugs, lady beetles and others.

Another positive attribute of substituted benzoylureas of structural formula (I) for controlling beet armyworm on cotton is its long residual effect on the leaf. It resists wash-off and its effectiveness is not diminished by sunlight. Use of substituted benzoylureas of structural formula (I) also delays and diminishes the use of pesticides which are more toxic to beneficials.

SUMMARY OF THE INVENTION

Substituted benzoylureas of structural formula (I) are active on other foliar feeding insects which are not controlled by the Bt toxin of this cotton variety. It was surprisingly discovered that the control of beet armyworm by substituted benzoylureas of structural formula (I) was greatly enhanced on Bt cotton versus cotton not having that gene.

This invention discloses a method for controlling insects of Lepidoptera on a genetically altered cotton plant having incorporated therein a gene derived from *Bacillus thuringiensis* (Bt) which codes for and expresses a protein having pesticide activity comprising the steps of applying to the foliage of said genetically altered cotton plant a pesticidally active amount of a substituted benzoyl urea represented by structural formula:

(I)

[Chemical structure: benzene ring with substituents A and B, connected to -C(=X)-N(R)-C(=Y)-N(R$_2$)-R$_1$]

where
- A is a hydrogen atom, a halogen atom, a methyl group or a methoxy group,
- B also represents a hydrogen atom, a halogen atom, a methyl group or a methoxy group, X and Y each represent an oxygen atom or a sulfur atom,
- R is a hydrogen atom, an alkyl group, a hydroxy group, an alkoxy group, an alkoxymethyl group, an acyl group or an alkoxycarbonyl group,
- R$_1$ is a hydrogen atom, any molecule or group of molecules containing at least one carbon atom, preferably, an alkyl group unsubstituted or substituted with halogen, with alkoxy, with alkylthio or with cyano, a 1-cycloalkenyl group, a benzyl group unsubstituted or substituted with halogen, a hydroxy group, an alkoxy group, an acyl group, an alkoxycarbonyl group, an alkoxythiocarbonyl group, an alkylsulfonyl group or a phenylsulfonyl group, while furthermore R and $R_1$ together with the group:

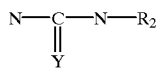

indicated in the above formula may form a ring system, and
$R_2$ represents a substituted or non-substituted phenyl group or a pyridyl group unsubstituted or substituted with halogen, with nitrocyano or with halogenated alkyl, wherein said ring system is represented by any of the following formulae:

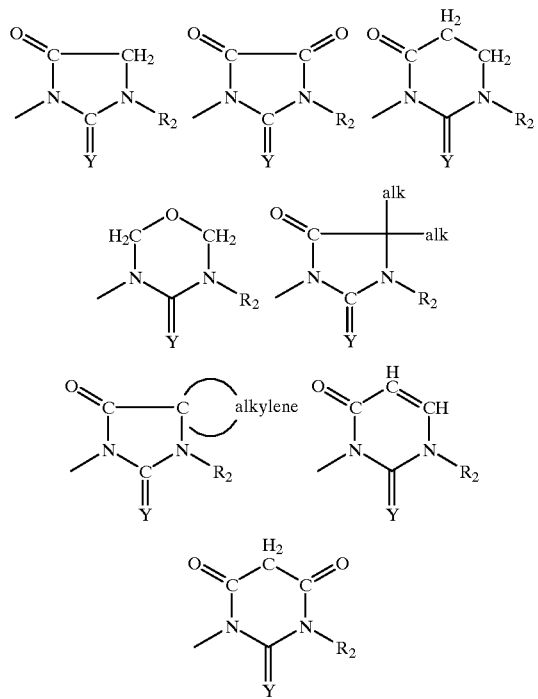

wherein the formulae Y and $R_2$ have the aforementioned meanings, alk is an alkyl group and alkylene is a bivalent saturated alkylene group, if $R_2$ is a substituted phenyl group, the phenyl group contains at least one substituent chosen from the group consisting of:
(a) 1–3 halogen atoms,
(b) 1–2 alkyl groups, unsubstituted or substituted with halogen, hydroxy, alkoxy, alkylthio, dialkyl amino, alkylsulphonyl and phenyl,
(c) tri- or tetramethylene,
(d) a cycloalkyl group, unsubstituted or substituted with halogen or cyano,
(e) 1–2 nitro groups or cyano groups or alkoxy groups,
(f) a dioxymethylene or dioxyethylene group,
(g) an acyl group, unsubstituted or substituted with halogen,
(h) an alkyl sulfonyl, phenyl sulfonyl, alkylthio, phenylthio or phenoxy group, unsubstituted or substituted with halogen,
(I) a sulfonamide group, which may alkylated, and
(k) a phenyl group, unsubstituted or substituted with halogen, nitro, cyano and halogenated alkyl.

A more preferred subgenus of (I) of the formula:

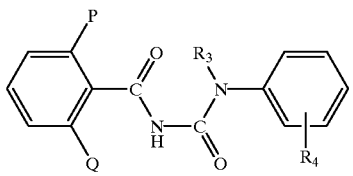

P and Q may be equal or different and each represent a chlorine atom, a fluorine atom or a methyl group, $R_3$ represents a hydrogen atom, an alkyl group, a benzyl group, an acyl group or an alkoxycarbonyl group, $R_4$ represents from 0–3 substituents selected from the group comprising from 1 to 3 halogen atoms, an alkyl group which contains from 1 to 15 carbon atoms and may be substituted with one or more halogen atoms or with a phenyl group, a cycloalkyl group unsubstituted or substituted with at least one halogen atom a nitro group, a cyano group, a phenyl group, a thiophenyl group, a benzoyl group, a thioalkyl group and an alkylsulfonyl group.

A still more preferred set substituted benzoyl urea is of the formula:

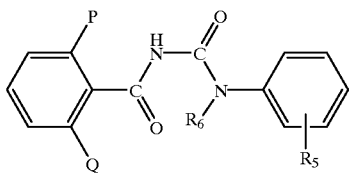

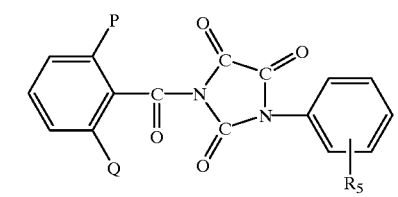

where

P and Q may be equal or different and each represent a chlorine atom, a fluorine atom or a methyl group, $R_6$ is a hydrogen atom or a lower alkyl group and $R_5$ represents 1–3 substituents selected from the group comprising 1–3 halogen atoms, an alkyl group which contains from 1 to 15 carbon atoms unsubstituted or substituted with at least one halogen atom, and a cycloalkyl group unsubstituted or substituted with at least one halogen atom, preferably $R_5$ represents one or two substituents in the position 3 or the position 4 or the positions 3 and 4 of the phenyl group.

Also preferred substituted benzoyl urea of the formulae:

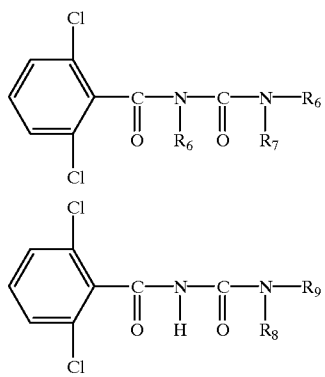

where $R_6$ is a hydrogen atom or a lower alkyl group, $R_7$ represents a unsubstituted or substituted phenyl group, $R_9$ is a hydrogen atom or a methyl group, $R_8$ represents a phenyl group unsubstituted or substituted with 1–3 halogen atoms, an alkyl group, cyclo-alkyl group, nitro group, tetramethylene group, methylenedioxy group or a methylsulfonyl group.

Yet another aspect of the invention is a method of protecting cotton throughout the growing season without the use of use of insecticides which kill beneficial insects comprising the steps of: a) planting a cotton seed pretreated with an effective amount of a pesticidal seed coating comprising pesticidally effective amounts of a fungicide or an insecticide, said cotton seed being the seed of a genetically altered cotton plant with a gene derived from *Bacillus thuringiensis* (Bt) which codes for and expresses a protein having pesticide activity cotton seed; b) germinating and growing said seed to form foliage; and c) applying to the foliage of said genetically altered cotton plants a pesticidally active amount of a benzoyl urea represented by structural formula (I).

DETAILED DESCRIPTION OF THE INVENTION

Substituted benzoylureas of structural formula (I) and other IGR's listed in Table A some of which are outside of the structural of formula (I) all act by interfering with the deposition of chitin, one of the main components of the insect exoskeleton.

TABLE A

| Common Chemical Name | Description |
| --- | --- |
| novaluron | N-((((3-chloro-4-(1,1,2-trifloro-2-trifloromthoxy)ethoxy)phenyl)amino)carbonyl)-2,6-diflorobenzamide, |
| flucycloxuron | 1-[α-(4-chloro-α-cyclopropylbenzylideneamino-oxy)-p-tolyl]-3-(2,6-difluorobenzoyl)urea |
| chlorfluazuron | 1-[3,5-dichloro-4-(3-chloro-5-trifluoromethyl-2-pyridyloxy)phenyl]-3-(2,6-difluorobenzoyl)urea |
| flufenozuron | 1-[4-(2-chloro-α,α,α-trifluoro-p-tolyloxy)-2-fluorophenyl]-3-(2,6-difluorobenzoyl)urea |
| teflubenzuron | 1-(3,5-dichloro-2,4-difluorophenyl)-3-(2,6-difluorobenzoyl)urea |

TABLE A-continued

| Common Chemical Name | Description |
| --- | --- |
| triflumuron | 1-(2-chlorobenzoyl)-3-(4-trifluoromethoxyphenyl)urea |
| hexaflumuron | 1-[3,5-dichloro-4-(1,1,2,2-tetrafluoroethoxy)phenyl]-3-(2,6-difluorobenzoyl)urea |
| lufenuron | N-[2,5-dichloro-4-(1,1,2,3,3,3-hexafluoropropoxy)-phenylaminocarbonyl]-2,6-difluorobenzamide |

Diflubenzuron represents one of most active structures. It belongs to the substituted 1-benzoyl-3-phenylurea family of pesticides, having the following structure.

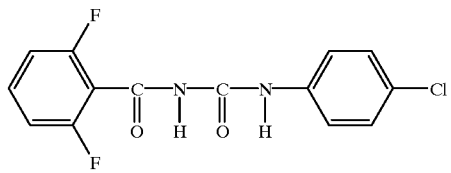

After treatment with substituted benzoylureas of structural formula (I) or Table A IGR's, the pest larvae have difficulties with the molting process. This results in a failure to successfully cast off the old exoskeleton and leads to the eventual death of the larva. The mode of action of substituted benzoylureas of structural formula (I) also gives rise to trans-ovarial effects by interfering with chitin deposition of the developing larva inside the egg. The compound is not plant systemic and does not penetrate the plant tissue. Therefore, sucking insects will not usually be affected.

Substituted benzoylureas of structural formula (I) provide excellent control of a number of important insect pests in a variety of fruit, field, pasture, turf, and horticulture crops. Of particular interest in this invention is cotton. Of even further interest is the beet armyworm as a pest in cotton.

As has been stated, there has been established and made commercially available genetically engineered cotton variety with particular activity on *Heliothis virescens* (tobacco budworm), *Helicoverpa zea* (cotton bollworm), *Pectinophora gossypiella* (pink bollworm), *Helicoverpa punctigera*, and *Helicoverpa armigera*. These transgenic cotton varieties possess a microbially derived gene derived from *Bacillus thuringiensis* (Bt). One cotton species is, for example, available under the tradename NuCOTN 33B® from the Monsanto Corporation. The term, Bt cotton, as used herein shall refer to any genetically engineered cotton varieties, either those currently available such as those described in U.S. Pat. No. 5,322,938 to McPherson et al which has a gene derived from *Bacillus thuringiensis* (Bt) which codes for a protein having pesticide activity, or any newer varieties that may be later developed, commercialized or disclosed.

Especially preferred benzoyl ureas are the following:
N-(2,6-dichlorobenzoyl)-N'-(3,4-dichlorophenyl)urea,
N-(2,6-difluorobenzoyl)-N'-(3,4-dichlorophenyl)urea,
N-(2,6-dimethylbenzoyl)-N'-(3,4-dichlorophenyl)urea,
N-(2,6-dichlorobenzoyl)-N'-(4-chlorophenyl)urea,
N-(2,6-dimethylbenzoyl)-N'-(4-chlorophenyl)urea,
N-(2,6-dichlorobenzoyl)-N'-(2,4-dichlorophenyl)urea,
N-(2,6-dichlorobenzoyl)-N'-(4-cyclopropylphenyl)urea,
N-(2,6-dichlorobenzoyl)-N'-(3-chloro-4-iodophenyl)urea,
N-(2,6-dichlorobenzoyl)-N'-(3-chloro-4-bromophenyl)urea,
N-(2,6-dichlorobenzoyl)-N'-(4-isopropylphenyl)urea,
N-(2,6-dichlorobenzoyl)-N'-(3,4-dibromophenyl)urea,
N-(2,6-dichlorobenzoyl)-N'-(4-fluorophenyl)urea, N-(2,6-dichlorobenzoyl)-N'-(3-trifluoromethylphenyl)urea,
N-(2,6-dichlorobenzoyl)-N'-(4-n-butylphenyl)urea,
N-(2,6-dichlorobenzoyl)-N'-(3-chloro-4-methylsulfonylphenyl)urea,
N-(2,6-dichlorobenzoyl)-N'-(4-t-butylphenyl)urea,
N-(2,6-dichlorobenzoyl)-N'-(3,4-difluorophenyl)urea,
N-(2,6-dichlorobenzoyl)-N'-(2,4-difluorophenyl)urea,
N-(2,6-dichlorobenzoyl)-N'-(4-bromophenyl)urea,
N-(2,6-dichlorobenzoyl)-N'-(2,5-difluoro-4-bromophenyl) urea,
N-(2,6-dichlorobenzoyl)-N'-(4-iodophenyl)urea,
N-(2,6-dichlorobenzoyl)-N'-(3-fluoro-4-chlorophenyl)urea,
N-(2,6-dichlorobenzoyl)-N'-(4-phenylphenyl)urea,
N-(2,6-dichlorobenzoyl)-N'-(4-cyanophenyl)urea,
N-(2,6-dichlorobenzoyl)-N'-(3-fluoro-4-bromophenyl)urea,
N-(2,6-dichlorobenzoyl)-N'-(3-fluoro-4-iodophenyl)urea,
N-(2,6-dichlorobenzoyl)-N'-(2-fluoro-4-iodophenyl)urea,
N-(2,6-dichlorobenzoyl)-N'-(4-n-propylphenyl)urea,
N-(2,6-dichlorobenzoyl)-N'-(4-trifluoromethylphenyl)urea,
N-(2,6-dichlorobenzoyl)-N'-(3-cyclopropylphenyl)urea,
N-(2,6-dichlorobenzoyl)-N'-(2-methyl-4-chlorophenyl) urea,
N-(2,6-dichlorobenzoyl)-N'-(4-iso-butylphenyl)urea,
N-(2,6-dichlorobenzoyl)-N'-(4-ethylphenyl)urea,
N-(2,6-dichlorobenzoyl)-N'-(4-n-dodecylphenyl)urea,
N-(2,6-dichlorobenzoyl)-N'-4-benzylphenyl)urea,
N-(2,6-dibromobenzoyl)-N'-(3,4-dichlorophenyl)urea,
N-(2,6-dichlorobenzoyl)-N'-(methyl)-N'-(3,4-dichlorophenyl)urea,
N-(2,6-dichlorobenzoyl)-N'-(ethyl)-N'-(3,4-dichlorophenyl) urea,
N-(2,6-dichlorobenzoyl)-N'-(methyl)-N'-(4-t.butylphenyl) urea,
N-(2,6-dichlorobenzoyl)-N'-(methyl)-(4-bromophenyl)urea,
N-(2,6-dichlorobenzoyl)-N'-(ethyl)-N'-(4-bromophenyl) urea,
N-(2,6-dichlorobenzoyl)-N'-(ethyl)-N'-4-isopropylphenyl) urea,
N-(2,6-dichlorobenzoyl)-N'-(ethyl)-N'-(4-n-butylphenyl) urea,
N-(2,6-dichlorobenzoyl)-N'-(methyl)-N'-(4-chlorophenyl) urea,
N-(2,6-dichlorobenzoyl)-N'-(ethyl)-N'-(4-chlorophenyl) urea,
N-(2,6-dichlorobenzoyl)-N'-(ethyl)-N'-(4-t.butylphenyl) urea,
N-(2,6-dichlorobenzoyl)-N'-(methyl)-N'-(4-nitrophenyl) urea,
3-(2,6-dichlorobenzoyl)-1-(4-chlorophenyl)-parabanic acid
N-(2,6-dichlorobenzoyl)-N'-(2,4,5-trichlorophenyl)urea,
N-(2,6-dichlorobenzoyl)-N'-(phenyl)urea,
N-(2,6-dichlorobenzoyl)-N'-(4-nitrophenyl)urea,
N-(2,6-difluorobenzoyl)-N'-(4-trifluoromethylphenyl)urea,
N-(2,6-difluorobenzoyl)-N'-(4-n-butylphenyl)urea,
N-(2,6-difluorobenzoyl)-N'-(4-t.butylphenyl)urea,
w-(2,6-difluorobenzoyl)-N'-(4-isopropylphenyl)urea,
N-(2,6-difluorobenzoyl)-N'-(3-fluoro-4-iodobenzyl)urea,
N-(2,6-difluorobenzoyl)-N'-(3-fluoro-4-chlorophenyl)urea,
N-(2,6-difluorobenzoyl)-N'-(3-trifluoromethylphenyl)urea,
N-(2,6-difluorobenzoyl)-N'-(4-isobutylphenyl)-N'-(methyl) urea
N-(2,6-difluorobenzoyl)-N'-(4-chlorophenyl)urea,
N-(2,6-difluorobenzoyl)-N'-(4-bromophenyl)urea,
N-(2,6-difluorobenzoyl)-N'-(4-fluorophenyl)urea,
N-(2,6-difluorobenzoyl)-N'-(4-thiomethylphenyl)urea,
N-(2,6-difluorbenzoyl)-N'-(methyl)-N'-(4-chlorophenyl) urea, and
N-(2,6-difluorbenzoyl)-N-(methoxymethyl)-N'-(3,4-dichlorophenyl)urea.

Formulation of Active Ingredients

The benzoyl ureas of formula (I) or Table A may be formulated as required with a suitable carrier.

Suitable carriers for the present compositions are wide ranging. The carrier may be a solid, for example, finely divided particulate solids, granules, pellets, wettable powders, soluble powders and the like. Among the solid carriers within the contemplation of the subject invention are such organic and inorganic materials as attapulgite clay, sand, vermiculite, corncob, activated carbon and mineral silicates. Among the mineral silicates preferred for use in the composition of the present invention are mica, talc, pyrophyllite, clays and the like.

A solid composition may be prepared from a solid carrier, such as one of those described immediately above. In that case, the active ingredient is impregnated onto the solid carrier. Alternatively, the active ingredient may be formulated into a wettable powder by grinding it into a fine powder and mixing it with the solid carrier to which a surface active dispersing agent has been added. The wettable powder is then dispersed in water and applied as a dispersion.

Indeed, the above described dispersion is representative of a composition which may also be classified as a liquid composition. In addition to liquid dispersions, the liquid composition may be in the form of a solution or an emulsion. In the case of a liquid solution, the active ingredient is dissolved in an aqueous or organic solvent. In most cases the solvent, which acts as the carrier, is organic. In addition to aromatic hydrocarbons, such as toluene and xylene, other preferred solvents include such organic compounds as acetone, methanol, isopropanol, t-butyl alcohol, cyclohexanone, dioxane, dimethylformamide, dimethyl sulfoxide, ethylene dichloride, diacetone alcohol and N-methylpyrrolidone.

A water emulsion, another preferred embodiment of a liquid composition within the contemplation of the present invention, is prepared from a solution, as described above, to which a surface active agent is added. Surface active agents suitable for use in forming an emulsion within the contemplation of this invention are known to those skilled in the art. *McCutcheon's Detergents and Emulsifiers*, Allured Publishing Corp., Ridgewood, N.J. (1970); U.S. Pat. No. 2,514,916, at Columns 2 to 4; and U.S. Pat. No. 2,547,734, at Columns 3 and 4, provide detailed examples of such surface active agents suitable for this purpose. As indicated in these references, the surface active agent may be anionic, non-ionic or cationic.

In yet another embodiment, the carrier may be an aerosol. To prepare an aerosol, the active ingredient is dissolved in a first solvent. This first solvent is conventional in the sense that although it is volatile, it is not highly volatile. This solution is then admixed with a highly volatile solvent, a so-called liquid aerosol carrier. The aerosol carrier is liquid only under elevated pressure. At ambient temperature and pressure, the aerosol carrier is a gas. In a subembodiment of this preferred carrier, the aerosol carrier may itself be active.

The substituted benzoylurea is formulated as the active ingredient at weight percents of from 10 to 90 percent, preferably 20 to 80 and most preferably at 25 to 60 percent with the remainder being carriers as described in the section just above. This formulated product is then further diluted with water to create the appropriate dilution to be applied in the field at a rate from about 0.01 grams of active ingredient (a.i.) per hectare (g/ha) to about 500 g of a.i./ha, preferably 5 to 400 g of a.i./ha and most preferably 25 to 300 g of a.i./ha of active ingredient.

EXAMPLES

In the experimental section which follows, tests performed using diflubenzuron on both NuCOTN 33B and non-transgenic cotton, exemplified by Stoneville 453, to control the beet armyworm shows the synergy between diflubenzuron and Bt cotton. Again, it must be re-emphasized that Bt cotton has previously been said to have no major pesticidal effect on beet armyworm. Diflubenzuron is represented by the structural formula:

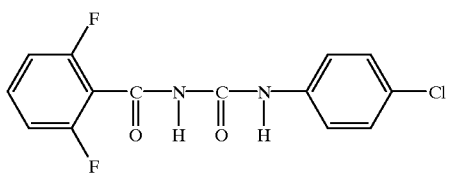

In the following procedure, the insecticide formulation used was the commercial product, Dimilin 2L, commercially available from Uniroyal Chemical Company, Inc. This formulation contains 2 pounds of active ingredient diflubenzuron per gallon of product. This formulated form of product is then further diluted with water to arrive at the dosage, expressed in grams of active ingredient per hectare.

For beet armyworm bioassay, eggs (1000) of beet armyworm (*Spodoptera exigua*) were received from the USDA-ARS Southern Crop Insect Management Laboratory, Stoneville, Miss. on cheesecloth. They were brushed off into cells of two diet trays containing tobacco budworm diet, and incubated until use at the early third instar stage. The time for development was usually eight days at 27° C.

Cotton plants were started four weeks prior to bioassay. Stoneville and NuCOTN seeds were planted at 3/pot in 4 inch azalea pots and allowed to germinate and develop on a heated bench. Cotton plants were thinned to one plant per pot and cultured in a greenhouse to the 4 true-leaf stage. Before treatment, all plants were stripped of foliage except for the 2 most recent expanded leaves.

Diflubenzuron applications at 0.03, 0.125, and 0.5 ounces of Dimilin 2L/acre (oz/A) [which converts to 0.55, 2.12 and 8.75 grams a.i./ha respectively] were made in a trolley sprayer. The sprayer delivered an aqueous volume of 20 gallons per acre at 22 psi from a flat fan 8002E nozzle.

The bioassay was started once the leaf tissue had dried. Five third instar stage beet armyworm larvae were placed onto a single excised leaf resting on a moist filter paper in a petri dish. There were 8 replicates per treatment. Placement of the dishes in an incubator at 27° C. represented 0 days after treatment (DAT). Leaves in the bioassay were replaced according to treatment group as they approached complete consumption. The amount of consumption was thus reported as units of leaf consumption, with 100 units equal to 100% damage to one leaf. The number of survivors was determined at 3 or 4 days after treatment.

TABLE 1

Efficacy on Beet Armyworm of Diflubenzuron on Transgenic and Non-Transgenic Cotton

| Type of Cotton Plant/Dimilin 2L Concentration in ounces/acre | Units of Leaf Consumption at 3 Days | Mean Number of Larvae Alive at 3 Days |
|---|---|---|
| Stoneville/Untreated | 75.0 | 4.9 |
| Stoneville/8.75 g a.i./ha Diflubenzuron | 26.9 | 3.3 |

TABLE 1-continued

Efficacy on Beet Armyworm of Diflubenzuron on Transgenic and Non-Transgenic Cotton

| Type of Cotton Plant/Dimilin 2L Concentration in ounces/acre | Units of Leaf Consumption at 3 Days | Mean Number of Larvae Alive at 3 Days |
|---|---|---|
| NuCOTN/Untreated | 40.0 | 4.5 |
| NuCOTN/8.75 g a.i./ha Diflubenzuron | 16.0 | 2.1 |

TABLE 2

Efficacy on Beet Armyworm of Diflubenzuron on Transgenic and Non-Transgenic Cotton

| Type of Cotton Plant/Dimilin 2L Concentration in ounces/acre | Units of Leaf Consumption at 4 Days | Mean Number of Larvae Alive at 4 Days |
|---|---|---|
| Stoneville/Untreated | 110.6 | 4.6 |
| Stoneville/0.55 g a.i./ha Diflubenzuron | 87.5 | 3.6 |
| Stoneville/2.12 g a.i./ha Diflubenzuron | 106.3 | 3.9 |
| NuCOTN/Untreated | 58.1 | 3.6 |
| NuCOTN/0.55 g/ha Diflubenzuron | 30.0 | 2.4 |
| NuCOTN/2.12 g/ha Diflubenzuron | 24.4 | 1.9 |

It is apparent that various modifications may be made in the formulations, active ingredients and application of the synergistic combinations of this invention without departing from the inventive concepts herein as defined in the claims.

We claim:

1. A method for controlling beet armyworms on a genetically altered cotton plant having incorporated therein a gene derived from *Bacillus thuringiensis* (Bt) which codes for and expresses a protein having pesticide activity comprising the steps of:

applying to the foliage of said genetically altered cotton plant an enhanced pesticidally active amount of a substituted benzoyl urea represented by a structural formula selected from the group consisting of:

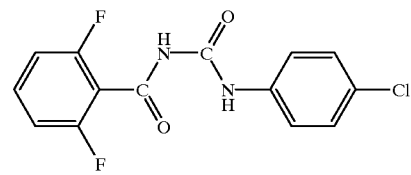

and

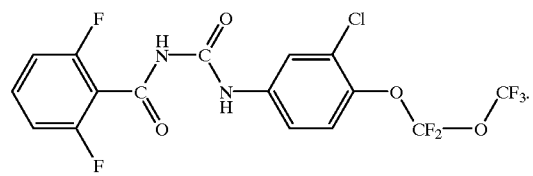

2. The method of claim 1 wherein the substituted benzoyl urea is represented by the structural formula:

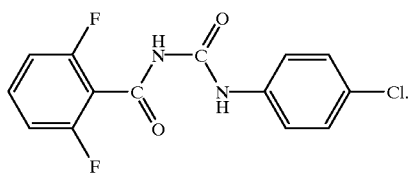

3. The method of claim 1 wherein the substituted benzoyl urea is applied in the field at a rate of from about 0.01 gram active ingredient per hectare to about 500 grams per hectare.

4. The method of claim 2 wherein the substituted benzoyl urea is applied in the field at a rate of from about 0.01 gram active ingredient per hectare to about 500 grams per hectare.

5. A method of protecting cotton from beet armyworms throughout the growing season without the use of insecticides that kill beneficial insects comprising the steps of:

a) planting a cotton seed pretreated with an effective amount of a pesticidal seed coating comprising pesticidally effective amounts of a fungicide or an insecticide, said cotton seed being the seed of a genetically altered cotton plant with a gene derived from *Bacillus thuringiensis* (Bt) which codes for and expresses a protein having pesticide activity;

b) germinating and growing said seed to form foliage; and c) applying to the foliage of said genetically altered cotton plant an enhanced pesticidally active amount of a substituted benzoyl urea represented by a structural formula selected from the group consisting of:

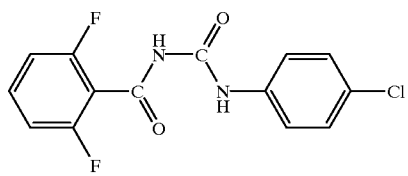

and

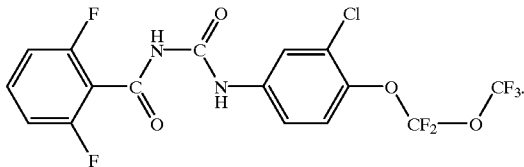

6. The method of claim 5 wherein the substituted benzoyl urea is represented by the structural formula:

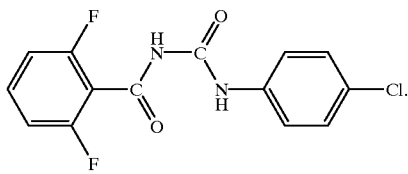

7. The method of claim 5 wherein the substituted benzoyl urea is applied in the field at a rate of from about 0.01 gram active ingredient per hectare to about 500 grams per hectare.

8. The method of claim 6 wherein the substituted benzoyl urea is applied in the field at a rate of from about 0.01 gram active ingredient per hectare to about 500 grams per hectare.

* * * * *